United States Patent
Hwang et al.

(10) Patent No.: US 10,435,459 B2
(45) Date of Patent: Oct. 8, 2019

(54) USE OF A LONG ACTING GLP-1/GLUCAGON RECEPTOR DUAL AGONIST FOR THE TREATMENT OF NON-ALCOHOLIC FATTY LIVER DISEASE

(71) Applicant: HANMI PHARM. CO., LTD., Gyeonggi-do (KR)

(72) Inventors: Sang Youn Hwang, Gyeonggi-do (KR); Jin Young Kim, Gangwon-do (KR); Seung Su Kim, Seoul (KR); In Young Choi, Gyeonggi-do (KR); Sung Youb Jung, Gyeonggi-do (KR); Se Chang Kwon, Seoul (KR)

(73) Assignee: Hanmi Pharm. Co., Ltd., Hwaseong-Si, Gyeonggi-Do (KR)

( * ) Notice: Subject to any disclaimer, the term of this patent is extended or adjusted under 35 U.S.C. 154(b) by 0 days.

(21) Appl. No.: 16/267,880

(22) Filed: Feb. 5, 2019

(65) Prior Publication Data
US 2019/0169271 A1  Jun. 6, 2019

Related U.S. Application Data

(63) Continuation of application No. 15/511,405, filed as application No. PCT/KR2015/009753 on Sep. 16, 2015, now Pat. No. 10,233,230.

(30) Foreign Application Priority Data

Sep. 16, 2014 (KR) .......................... 10-2014-0122862

(51) Int. Cl.
| | |
|---|---|
| A61K 38/00 | (2006.01) |
| C07K 16/00 | (2006.01) |
| A61K 38/26 | (2006.01) |
| A61K 47/60 | (2017.01) |
| A61K 47/68 | (2017.01) |
| A61K 49/00 | (2006.01) |

(52) U.S. Cl.
CPC .............. *C07K 16/00* (2013.01); *A61K 38/26* (2013.01); *A61K 47/60* (2017.08); *A61K 47/6811* (2017.08); *A61K 49/0008* (2013.01); *C07K 2317/41* (2013.01); *C07K 2317/53* (2013.01)

(58) Field of Classification Search
None
See application file for complete search history.

(56) References Cited

U.S. PATENT DOCUMENTS

| | | | |
|---|---|---|---|
| 6,776,983 B1 | 8/2004 | Sumida et al. |
| 7,217,845 B2 | 5/2007 | Rosen et al. |
| 7,521,424 B2 | 4/2009 | Rosen et al. |
| 7,737,260 B2 | 6/2010 | Kim et al. |
| 7,928,058 B2 | 4/2011 | Sinha et al. |
| 8,263,084 B2 | 9/2012 | Song et al. |
| 8,729,017 B2 | 5/2014 | Dimarchi et al. |
| 8,778,872 B2 | 7/2014 | Dimarchi et al. |
| 8,975,001 B2 | 3/2015 | Bae |
| 9,522,946 B2 | 12/2016 | Jung et al. |
| 9,731,031 B2 | 8/2017 | Jung et al. |
| 9,765,131 B2 | 9/2017 | Jung et al. |
| 2003/0032588 A1 | 2/2003 | Marshall et al. |
| 2004/0087778 A1 | 5/2004 | Feige et al. |
| 2006/0269553 A1 | 11/2006 | Kim et al. |
| 2009/0053246 A1 | 2/2009 | Kim et al. |
| 2009/0238838 A1 | 9/2009 | Kim et al. |
| 2009/0297496 A1 | 12/2009 | Grabowski |
| 2009/0298757 A1 | 12/2009 | Bloom et al. |
| 2010/0144617 A1 | 6/2010 | Sinha Roy et al. |
| 2010/0190701 A1 | 7/2010 | Day et al. |
| 2010/0196405 A1 | 8/2010 | Ng |
| 2010/0330108 A1 | 12/2010 | Song et al. |
| 2011/0034374 A1 | 2/2011 | Bloom et al. |
| 2011/0065633 A1 | 3/2011 | Dimarchi et al. |
| 2011/0152182 A1 | 6/2011 | Alsina-Fernandez et al. |
| 2011/0190200 A1 | 8/2011 | Dimarchi et al. |
| 2012/0003712 A1 | 1/2012 | Song et al. |
| 2012/0165503 A1 | 6/2012 | Carrington et al. |
| 2012/0178670 A1 | 7/2012 | Riber et al. |
| 2012/0329707 A1 | 12/2012 | Dimarchi et al. |

(Continued)

FOREIGN PATENT DOCUMENTS

| | | |
|---|---|---|
| CN | 101213209 A | 7/2008 |
| CN | 101389648 A | 3/2009 |

(Continued)

OTHER PUBLICATIONS

US 8,729,011 B2, 05/2014, Dimarchi (withdrawn)
Xu et al., "SIRT1 mediates the effect of GLP-1 receptor agonist exenatide on ameliorating hepatic steatosis", Diabetes, Jun. 19, 2014, vol. 63, No. 11, 3637-3646.
Zhou et al., "Role of AMP-activated protein kinase in mechanism of metformin action", J. Clinical Invest., 2001, 108, 1167-1174.
Wynne et al., "Oxyntomodulin increases energy expediture in addition to decreasing energy intake in overweight and obese humans: a randomised controlled trial," International Journal of Obesity, 2006, 30, 1729-1736.

(Continued)

*Primary Examiner* — Jeanette M Lieb
(74) *Attorney, Agent, or Firm* — BakerHostetler

(57) ABSTRACT

The present invention relates to a pharmaceutical composition for the prevention or treatment of non-alcoholic fatty liver disease including a long-acting GLP-1/glucagon receptor dual agonist, and a method for preventing or treatment of non-alcoholic fatty liver disease including administering the composition. The composition of the present invention either has no side effect of weight gain or reduces the side effect of weight gain, which is a side-effect of conventional therapeutic agents for non-alcoholic fatty liver disease, and reduces the amount of administrations of a long-acting GLP-1/glucagon receptor dual agonist, thus greatly improving patient's convenience. In addition, the long-acting GLP-1/glucagon receptor dual agonist of the present invention improves in vivo sustainability and stability.

13 Claims, 3 Drawing Sheets

Specification includes a Sequence Listing.

(56) References Cited

U.S. PATENT DOCUMENTS

| | | |
|---|---|---|
| 2013/0035285 A1 | 2/2013 | Lau et al. |
| 2013/0122023 A1 | 5/2013 | Woo et al. |

FOREIGN PATENT DOCUMENTS

| | | |
|---|---|---|
| CN | 101578107 A | 11/2009 |
| CN | 101974077 A | 2/2011 |
| CN | 102010473 A | 4/2011 |
| CN | 102369209 A | 3/2012 |
| CN | 103732616 A | 4/2014 |
| CN | 103732618 A | 4/2014 |
| EP | 2300037 A2 | 3/2011 |
| EP | 2330124 A2 | 6/2011 |
| EP | 1891105 B1 | 4/2012 |
| EP | 2884994 A1 | 6/2015 |
| JP | 2003-531632 A | 10/2003 |
| JP | 2008-169195 A | 7/2008 |
| JP | 2008-543816 A | 12/2008 |
| JP | 2009-527558 A | 7/2009 |
| JP | 2009-203235 A | 9/2009 |
| JP | 2011-505355 A | 2/2011 |
| JP | 2011-511753 A | 4/2011 |
| JP | 2013-537525 A | 10/2013 |
| KR | 10-0389726 B1 | 6/2003 |
| KR | 10-2005-0026685 A | 3/2005 |
| KR | 10-2006-0106486 A | 10/2006 |
| KR | 10-2008-0039375 A | 5/2008 |
| KR | 10-2009-0096498 A | 9/2009 |
| KR | 10-2009-0098843 A | 9/2009 |
| KR | 10-0925017 B1 | 11/2009 |
| KR | 10-2010-0043208 A | 4/2010 |
| KR | 10-2010-0105494 A | 9/2010 |
| KR | 10-2011-0039230 A | 4/2011 |
| KR | 10-2011-0056472 A | 5/2011 |
| KR | 10-2012-0043208 A | 5/2012 |
| KR | 10-2012-0052973 A | 5/2012 |
| KR | 10-2012-0137271 A | 12/2012 |
| KR | 10-2012-0139579 A | 12/2012 |
| KR | 10-2014-0018462 A | 2/2014 |
| NZ | 618811 A | 5/2016 |
| NZ | 718999 A | 7/2017 |
| TW | 200848423 A | 12/2008 |
| TW | 201245246 | 11/2012 |
| TW | 201546053 | 12/2015 |
| WO | 96/32478 A1 | 10/1996 |
| WO | 97/34631 A1 | 9/1997 |
| WO | 2003/022304 A1 | 3/2003 |
| WO | 2004/062685 A2 | 7/2004 |
| WO | 2005/035761 A1 | 4/2005 |
| WO | 2005/087797 A1 | 9/2005 |
| WO | 2006/059106 A2 | 6/2006 |
| WO | 2006/086769 A2 | 8/2006 |
| WO | 2006/107124 A1 | 10/2006 |
| WO | 2006/134340 A2 | 12/2006 |
| WO | 2007/022123 A2 | 2/2007 |
| WO | 2007/100535 A2 | 9/2007 |
| WO | 2007/146038 A2 | 12/2007 |
| WO | 2008/071972 A1 | 6/2008 |
| WO | 2008/082274 A1 | 7/2008 |
| WO | 2008/101017 A2 | 8/2008 |
| WO | 2009/033756 A2 | 3/2009 |
| WO | 2009/058734 A1 | 5/2009 |
| WO | 2009/069983 A2 | 6/2009 |
| WO | 2009/099763 A1 | 8/2009 |
| WO | 2009/155257 A1 | 12/2009 |
| WO | 2009/155258 A2 | 12/2009 |
| WO | 2013/192129 A1 | 12/2009 |
| WO | 2010/013012 A2 | 2/2010 |
| WO | 2010/033207 A1 | 3/2010 |
| WO | 2010/033220 A2 | 3/2010 |
| WO | 2010/071807 A1 | 6/2010 |
| WO | 20101070253 A1 | 6/2010 |
| WO | 20101096052 A1 | 8/2010 |
| WO | 20101096142 A1 | 8/2010 |
| WO | 2010/107256 A2 | 9/2010 |
| WO | 2010/108153 A2 | 9/2010 |
| WO | 2010/148089 A1 | 12/2010 |
| WO | 2011/006497 A1 | 1/2011 |
| WO | 2011/056713 A2 | 5/2011 |
| WO | 2011/071957 A1 | 6/2011 |
| WO | 2011/075393 A2 | 6/2011 |
| WO | 2011/087671 A1 | 7/2011 |
| WO | 2011/087672 A1 | 7/2011 |
| WO | 2011/143208 A1 | 11/2011 |
| WO | 2011/163012 A2 | 12/2011 |
| WO | 2012/008779 A1 | 1/2012 |
| WO | 2012/011752 A2 | 1/2012 |
| WO | 2012/057525 A2 | 5/2012 |
| WO | 2012/088379 A2 | 6/2012 |
| WO | 2012/169798 A2 | 12/2012 |
| WO | 2012/173422 A1 | 12/2012 |
| WO | 2013/133667 A1 | 9/2013 |
| WO | 2013/157002 A1 | 10/2013 |
| WO | 2014/017843 A1 | 1/2014 |
| WO | 2014/017853 A2 | 1/2014 |
| WO | 2014/049610 A2 | 4/2014 |
| WO | 2014/073842 A1 | 5/2014 |
| WO | 2014/073845 A1 | 5/2014 |

OTHER PUBLICATIONS

Wynne et al, "Subcutaneous Oxyntomodulin Reduces Body Weight in Overweight and Obese Subjects a Double-Blind, Randomized, Controlled Trial", Diabetes, Aug. 2005, vol. 54, pp. 2390-2395.
World Health Organization, Global Strategy on Diet, Physical Activity and Health, 2004.
What Causes Overweight and Obesity?, from http://www.nhlbi.nih.gov/health/health-topics/topics/obe/causes.html, pp. 1-5, accessed Oct. 6, 2014.
Water, from http://www.biology-online.org/dictionary/Water, pp. 1-3, accessed Apr. 24, 2014.
Voet et al., "Abnormal Hemoglobins", Biochemistry, John Wiley & Sons Inc., 1995, 235-241.
Vitamins & Supplements Search, http://www.webmd.com/vitamins-supplements/condition-1275-Hyperlipidemia.a- spx, accessed Dec. 29, 2015, pp. 1-3.
U.S. Appl. No. 14/748,389: Non-Final Rejection, dated Jan. 13, 2016, 18 pages.
U.S. Appl. No. 14/126,914: Non-Final Rejection, dated Mar. 5, 2015, 35 pages.
U.S. Appl. No. 14/126,914: Communication, dated Sep. 18, 2014, 14 pages.
U.S. Appl. No. 14/124,969: Non-Final Rejection dated Dec. 10, 2014, 40 pages.
U.S. Appl. No. 14/124,969: Final Rejection dated Apr. 14, 2015, 17 pages.
Treethammathurot et al., "Effect of PEG molecular weight and linking chemistry on the biological activity and thermal stability of PEGylated trypsin", International Journal of Pharmaceutics, 2008, vol. 357, pp. 252-259.
Taiwanese Patent Office, Communication dated Mar. 11, 2014 issued in corresponding Tawinese Patent Application No. 101120633.
Taiwanese Intellectual Property Office, "Examination Report", dated Dec. 23, 2013 issued in corresponding application No. 101121483, 15 pages.
State Intellectual Property Office of PRC, English translation of communication dated Mar. 6, 2015, issued in corresponding Chinese Application No. 201280038851.4 (submitted without translation on Jun. 24, 2015).
State Intellectual Property Office of PRC, "Notification of Second Office Action", dated Sep. 15, 2015, issued in corresponding Chinese Application No. 201280038851A, 15 pages.
State Intellectual Property Office of PRC, "Notification of First Office Action", dated Jan. 7, 2015 issued in corresponding Chinese Application No. 201280039781.4, 21 pages.
Skosyrev et al., "The Dependence of Stability of the Green Fluorescent Protein—Obelin Hybrids on the Nature of Their Constituent Modules and the Structure of the Amino Acid Linker", Russian Journal of Bioorganic Chemistry, 2001, vol. 27, No. 5, pp. 323-329.

(56) References Cited

OTHER PUBLICATIONS

Sigma-Aldrich, "Exendin-4 sequence", http://www.simgaaldrich.com/catalog/product/sigma/e7144lang=en® ion=US, accessed Dec. 28, 2015, 1 page.
Shigeru, "Obesity and Metabolic Syndrome", Tokyo Internal Medical Association Seminar 2008 Special Lecture, Dec. 2008, vol. 24, No. 2, 8 pages.
Shani Ben-Shlomo et al., "Glucagon-like pepetide-1 reduces hepatic lipogenesis via activation of AMP-activated protein kinase", Journal of Hepatology, Sep. 27, 2010, vol. 54, No. 6, pp. 1214-1223.
Seok et al., "Exendin-4 Improves Nonalcoholic Fatty Liver Disease by Regulating Glucose Transporter 4 Expression in ob/ob Mice", Korean Journal of Physiology and Pharmacology, Jan. 1, 2014, p. 333.
Santoprete et al., "DPP-IV-resistant, long acting oxyntomodulin derivatives", Journal of Peptide Science, Feb. 2011, vol. 17, No. 4, 270-280.
Rudinger, "Characteristics of the amino acids as components of a peptide hormone sequence", Peptide Hormones, JA Parsons Ed., 1976, pp. 1-7.
Pocai et al., "Glucagon-like peptide 1/glucagon receptor dual agonism reverses obesity in mice", Diabetes, 2009, vol. 58, No. 10, 2253-2266.
Obesity Causes, from http://www.hsph.harvard.edu/obesity-prevention-source/obesity-causes/, pp. 1-3, accessed Oct. 6, 2014.
Ngo et al, Computational Complexity, Protein Structure Protection, and the Levinthal Paradox, 1994, pp. 491-494.
New Zealand Intellectual Property Office, "Further Examination Report", dated Oct. 30, 2015, issued in corresponding application No. 618810, 4 pages.
New Zealand Intellectual Property Office, "First Examination Report", dated Oct. 7, 2014, issued in corresponding application No. 618810, 3 pages.
Neuschwander-Tetri et al., "Improved Nonalcoholic Steatohepatitis After 48 Weeks of Treatment With the PPAR-y Ligand Rosiglitazone", Hepatology, 2003, 38, 1008-1017.
Merriam Webster, Dictionary: prophylactic, (3 pages total), accessed from the WWW on Feb. 8, 2015. (3pgs.) URL: http://www.merriam-webster.com/dictionary/prophylactic.
Lam, "Nonatheromatous Arteriosclerosis", http://222.merckmanuals.com/profession/cardiovasculardisorders/arterioscl-erosis/non . , accessed Dec. 29, 2015, 2 pages.
Lam, "Definition of Arteriosclerosis", http://www.merkmanuals.com/professional/cardiovascular-disorders/arterios-clerosis/defi . , accessed Dec. 29, 2015, 1 page.
Lam, "Atherosclerosis", Atherosclerosis—Cardiovascular Disorders—Merck Manuals Professional Edition, http://www.merkmanuals.com/professional/cardiovascular-disorder/arteriosc-lerosis/atherosclerosis, accessed Dec. 29, 2015, 1-14.
Korean Intellectual Property Office, "Notice of Preliminary Rejection", dated Nov. 20, 2014, issued in corresponding Korean Application No. 10-2012-0061166, 7 pages.
Kerr et al., "(D-Ser2)Oxm[mPEG-PAL]: A novel modified analogue of oxyntomodulin with antihyperglycaemic, insullinotropic and anorexigenic actions", Biochemical Pharmacology, Dec. 2010, vol. 80, Issue 11, 1727-1735.
Frankel et al., "Characterization of diphtheria fusion proteins targeted to the human interleukin-3 receptor", Protein Engineering, 2000, vol. 13, No. 8, pp. 575-581.
K Wynne et al., "Oxyntomodulin increases energy expenditure in addition to decreasing energy intake in overweight and obese humans: a randomised controlled trial", International Journal of Obesity (2006) 30, pp. 1729-1736.
Japan Patent Office, "Grounds for Rejection", dated Nov. 24, 2015, issued in corresponding Japanese Application No. 2014-514799, 9 pages.
Japan Patent Office, "Grounds for Rejection", dated Dec. 15, 2015, issued in corresponding Japanese Application 2014/515759, 12 pages.

International Patent Application No. PCT/KR2013/009990: International Search Report and Written Opinion dated Jan. 20, 2014, 12 pages.
International Patent Application No. PCT/KR2013/009986: International Search Report and Written Opinion dated Jan. 29, 2014, 11 pages.
International Patent Application No. PCT/KR2013/006668: International Search Report and Written Opinion dated Oct. 21, 2013, 10 pages.
International Patent Application No. PCT/KR2012/004722: International Search Report and Written Opinion dated Nov. 14, 2012, 6 pages.
Hepatitis Health Center, "Fatty Liver Disease", http://www.webmd.com/hepatitis/fatty-liver-diseasepage=2&print=true, accessed Dec. 29, 2015, pp. 1-4.
Habegger et al, The metabolic actions of glucagon revisited, Nat. Rev. Endocrinol., 2010, 6, pp. 689-697.
Goldberg, "Dyslipidemia", Dyslipidemia—Endocrine and Metabolic Disorders—Merck Manuals Professional Edition, http://www.merckmanuals.com/professional/endocrine-and-metabolic-diorders-/lipid-dis . , accessed Dec. 29, 2015, 11 pages.
European Patent Office, "Supplementary Partial European Search Report", dated Feb. 25, 2016, issued in counterpart Application No. 13823727.6, 7 pages.
European Patent Office, "Supplementary European Search Report", dated Oct. 13, 2014, issued in counterpart Application No. 12801247.3, 7 pages.
European Patent Office, "Supplementary European Search Report", dated Dec. 3, 2014, issued in counterpart Application No. 12797363.4, 5 pages.
English translation of Japanese Patent Application No. 2014-515759: Notice of Reason for Rejection dated Dec. 15, 2015, 5 pages.
English Translation of Chinese Patent Application No. 201280038851.4: Notification of Second Office Action dated Sep. 15, 2015, 9 pages.
Eaton, Hypolipemic action of glucagon in experimental endogenous lipemia in the rat, Journal of Lipid Research, 1973, 14, pp. 312-318.
Drucker, "Glucagon-Like Peptides", Diabetes, Feb. 1998, vol. 47, 159-169.
Ding et al, Exendin-4, a Glucagon-Like Protein-1 (GLP-1) Receptor Agonist, Reverses Hepatic Steatosis in ob/ob Mice, Hepatology, 2006, 43, pp. 173-181.
Diabetes, from http://www.merckmanuals.com/professional/endocrine-and-metabolic-disorders/ . . . , pp. 1-34, accessed Sep. 2, 2016.
Dhanesha et al., "Treatment with exendin-4 improves the antidiabetic efficacy and reverses hepatic steatosis in glucokinase activator treated db/db mice", European Journal of Pharmacology, vol. 714, No. 1, Jun. 25, 2013, pp. 188-192.
Definition of prophylactic, from http://www.merriam-webster.com/dictionary/prophylactic, pp. 1-3, accessed Feb. 8, 2015.
Day et al, Optimization of Co-Agonism at GLP-1 and Glucagon Receptors to Safely Maximize Weight Reduction in DIO-Rodents, Peptide Science, 2012, 98, pp. 443-450, published online Apr. 14, 2012.
Day et al, A new glucagon and GLP-1 co-agonist eliminates obesity in rodents, Nature Chemical Biology, 2009, 5, pp. 749-757.
Collie et al, Purification and sequence of rat oxyntomodulin, Proc. Natl. Acad. Sci. USA, 1994, 91, pp. 9362-9366.
Clark et al., "Identifying and Managing Patients with Hyperlipidemia", The American Journal of Managed Care, Aug. 1997, vol. 3, No. 8, 1211-1219.
Chao-lin Li et al., "Review on the effect of glucagon-like peptide-1 receptor agonists and dipeptidyl peptidase-4 inhibitors for the treatment of non-alcoholic fatty liver disease", Huashong University of Science and Technology Journal, vol. 35, No. 3, Jun. 1, 2015, pp. 333-336.
"Obesity", Merck Manual, http'://www.merckmanuals.com/professoinal/nutritional_disorders/obesity_and_the_metab., accessed Oct. 6, 2014, 1-9.

(56) References Cited

OTHER PUBLICATIONS

Bradley et al., Limits of Cooperativity in a Structurally Modular Protein: Response of the Notch Ankyrin Domain to Analogous Alanine Substitutions in Each Repeat, J. Mol. BloL (2002) 324, 373-386.

Berendsen, "A Glimpse of the Holy Grail?", Science, 1998, 282, 642-643.

"Prescription Medications for the Treatment of Obesity", U.S. Department of Health and Human Services, Apr. 2013, 1-8.

Park et al., "Dietary and Genetic Obesity Promote Liver Inflammation and Tumorigenesis by Enhancing IL-6 and TNF Expression", Cell, Jan. 22, 2010, 140, 197-208.

Eguchi et al., "Pilot study of liraglutide effects in non-alcoholic steatohepatitis and non-alcoholic fatty liver disease with glucose intolerance in Japanese patients (LEAN-J)", Hepatology Research, 2015, 45, 269-278.

Olaywi et al., "Novel anti-diabetic agents in non-alcoholic fatty liver disease: a mini-review", Hepatobiliary Pancreat Dis Int, Dec. 15, 2013, vol. 12, No. 6, 584-588.

Campbell et al., "Pharmacology, Physiology, and Mechanisms of Incretin Hormone Action", Cell Metabolism, Jun. 4, 2013, 17, 819-837.

```
                           SEQUENCE LISTING

<160> NUMBER OF SEQ ID NOS: 34

<210> SEQ ID NO 1
<211> LENGTH: 37
<212> TYPE: PRT
<213> ORGANISM: Homo sapiens
<220> FEATURE:
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
<212> TYPE: PRT
```

```
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
        35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
```

<223> OTHER INFORMATION: 4-imidazoacetyl

<400> SEQUENCE: 7

His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-Glu

<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Ser Lys
        35                  40

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
                20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 12

His Ser Gln Gly Thr Phe Thr Ser Asp Tyr Ser Arg Tyr Leu Asp Gly
1               5                   10                  15

Gly Gly His Gly Glu Gly Thr Phe Thr Ser Asp Leu Ser Lys Gln Met
                20                  25                  30

Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-Glu
<220> FEATURE:
<221> NAME/KEY: MOD_RES
<222> LOCATION: (20)..(20)
<223> OTHER INFORMATION: Alpha-methyl-Glu

<400> SEQUENCE: 13

His Ser Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-Glu
<220> FEATURE:
<221> NAME/KEY: MOD_RES
<222> LOCATION: (24)..(24)
<223> OTHER INFORMATION: Alpha-methyl-Glu

<400> SEQUENCE: 14

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-Glu

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly
1               5                   10                  15

Gly Gly His Ser Gln Gly Thr Phe Thr Ser Asp Leu Ser Arg Gln Leu
            20                  25                  30

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
        35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30

Arg Asn Asn Ile Ala
        35

```
<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20
```

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Ser Lys
        35                  40

```
<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 21
```

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
            20                  25                  30

Arg Asn Asn Ile Ala
        35

```
<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22
```

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys
            20                  25                  30

```
<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid

<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
```

<223> OTHER INFORMATION: Aminoisobutyric acid
<220> FEATURE:
<221> NAME/KEY: MISC_FEATURE
<222> LOCATION: (12)..(16)
<223> OTHER INFORMATION: Ring formation between residues

<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MISC_FEATURE
<222> LOCATION: (16)..(20)
<223> OTHER INFORMATION: Ring formation between residues

<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: D-Ser

<400> SEQUENCE: 29

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn

```
                    20                  25                  30

Arg Asn Asn Ile Ala
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: D-Ser

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aminoisobutyric acid

<400> SEQUENCE: 32

His Xaa Gln Gly Thr Phe Thr Ser Asp Tyr Ser Lys Tyr Leu Asp Glu
1               5                   10                  15
```

Lys Arg Ala Lys Glu Phe Val Gln Trp Leu Met Asn Thr Cys
                20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid

<400> SEQUENCE: 33

His Xaa Gln Gly Thr Phe Thr Ser Asp Tyr Ala Lys Tyr Leu Asp Glu
1               5                   10                  15

Lys Arg Ala Lys Glu Phe Val Gln Trp Leu Met Asn Thr Cys
                20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      oxyntomodulin derivative
<220> FEATURE:
<221> NAME/KEY: MOD_RES
<222> LOCATION: (2)..(2)
<223> OTHER INFORMATION: Aminoisobutyric acid

<400> SEQUENCE: 34

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
                20                  25                  30

USE OF A LONG ACTING GLP-1/GLUCAGON RECEPTOR DUAL AGONIST FOR THE TREATMENT OF NON-ALCOHOLIC FATTY LIVER DISEASE

CROSS-REFERENCE TO RELATED APPLICATIONS

This application is a continuation of U.S. Application No. 15/511,405 filed Mar. 15, 2017, which is the National Stage of International Application No. PCT/KR2015/009753 filed Sep. 16, 2015, which claims priority from Korean Patent Application No. 10-2014-0122862 filed Sep. 16, 2014, the disclosures of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 5, 2019, is named 106132.000301 SL.txt and is 19,372 bytes in size.

TECHNICAL FIELD

The present invention relates to a pharmaceutical composition for the prevention or treatment of non-alcoholic fatty liver disease, including a long-acting glucagon-like peptide-1 (GLP-1)/glucagon receptor dual agonist, and a method for preventing or treating non-alcoholic fatty liver disease including administering the composition.

BACKGROUND ART

Non-alcoholic fatty liver disease (NAFLD) is a type of a disease, showing histological organization similar to those of alcoholic liver disease, although is not associated with alcohol consumption, and is a kind of metabolic syndrome associated with non-alcoholic fatty liver (NAFL), non-alcoholic steatohepatitis (NASH), liver cirrhosis, and hepatocellular carcinomas. The occurrence of non-alcoholic fatty liver diseases increases with an increase in population with obesity and diabetes. In Korea, the annual incidence has reached approximately 16%.

Non-alcoholic fatty liver disease is known to be caused by various etiologies such as insulin resistance, lipotoxicity and inflammatory responses. Among them, the most common etiology is insulin resistance.

A lot of effort has been made to improve the insulin resistance to prevent/treat non-alcoholic fatty liver disease. For example, currently clinical trials for thiazolidnedinones (TZD) or metformin, a kind of insulin sensitizer, have been actively conducted (see, Hepatology (2003) 38: 1008-17, J Clin Invest (2001) 108: 1167-74).

However, in the case of treatment with the TZD-based drugs, there are disadvantages of a large weight gain and slow fluid flow, and thus the use of such treatment has been known to be impossible for patients with a heart disease. In addition to the TZD-based drugs, clinical tests using GLP-1 receptor agonists such as Victoza or Byetta for non-alcoholic fatty liver disease have been actively conducted. However, in these cases, the in vivo half-life is extremely short, and thus repeated administrations must be made once or at least twice per day, like other polypeptide hormones. Therefore, there is a disadvantage due to inconvenience to patients. Such frequent administrations cause great pain and discomfort to patients. That is, simply using general therapeutic agents for diabetes as a therapeutic agent for non-alcoholic fatty liver disease, through the mechanism of improving insulin resistance has disadvantages such as various side-effects or patient's inconvenience. Due to these factors, when a drug known to be effective in the treatment of diabetes, such as a drug for improving insulin resistance, is directly used as a therapeutic agent for non-alcoholic fatty liver disease, various factors which may result in problems such as side-effects have been known in the art. Hence, whether a drug known to be effective in the treatment of diabetes, such as a drug for improving insulin resistance, can definitely be used as a therapeutic agent for non-alcoholic fatty liver disease, is controversial. Thus, there still remains a need to develop drugs capable of treating non-alcoholic fatty liver disease while securing patient's convenience without side-effects.

DISCLOSURE OF INVENTION

Technical Problem

The present inventors have made many efforts to develop a drug for the prevention or treatment of non-alcoholic fatty liver disease, which maximizes patient's compliance while increasing the half life without side-effects such as body weight gain. As a result, the inventors have discovered that the in vivo half life of a long-acting GLP-1/glucagon receptor dual agonist linked to Fc fragment is greatly improved and also has an effective result of weight loss, and further liver triglyceride and blood cholesterol are decreased. The present invention has been completed on the basis of such discovery.

Solution to Problem

An objective of the present invention is to provide a pharmaceutical composition for the prevention or treatment of non-alcoholic fatty liver disease including a long-acting glucagon-like peptide-1 (GLP-1)/glucagon receptor dual agonist.

Another objective of the present invention is to provide a method for preventing or treating non-alcoholic fatty liver disease including administering the composition to a subject suspected of or having the non-alcoholic liver disease.

Advantageous Effects of Invention

The long-acting GLP-1/glucagon receptor dual agonist according to the present invention can widen the choices of patients by expanding the category of drugs which had until new been applicable to the non-alcoholic fatty liver disease, and increase patient's convenience by significantly increasing the blood half life. Further, the present invention provides a new alternative that can be applied without danger to patients with diseases other than non-alcoholic fatty liver disease through reduction of side-effects such as weight gain.

BEST MODE FOR CARRYING OUT THE INVENTION

In order to accomplish the objectives, one aspect of the present invention provides a pharmaceutical composition for prevention or treatment of non-alcoholic fatty liver disease comprising a long-acting glucagon-like peptide-1 (GLP-1)/glucagon receptor dual agonist.

The long-acting GLP-1/glucagon receptor dual agonist may be a long-acting GLP-1/glucagon receptor dual agonist which is in a conjugated form, wherein a biocompatible material or a carrier capable of increasing the duration of the activity of the dual agonist is linked to the agonist by a covalent bond or a linker.

In the case of treatment with TZD-based drugs, which are drugs for improving insulin response which is a mechanism for improving the insulin resistance, and conventional therapeutic agents of non-alcoholic fatty liver disease, there are disadvantages in that it was not possible for the treatment to apply to patients with heart diseases due to side-effects such as large weight gain and slow fluid flow. In the case of protein drugs such as peptide hormone, there are disadvantages in that the in vivo half life is short and thus repeated administration is necessary. The present inventors have discovered that the long-acting GLP-1/glucagon receptor dual agonist either has no side-effects of weight gain or reduces the side effect of weight gain in various animal models of non-alcoholic liver disease and that the long-acting GLP-1/glucagon receptor dual agonist can treat non-alcoholic fatty liver disease in a form in which sustainability in blood is dramatically increased. Accordingly, the present invention has been completed to provide the use of the long-acting GLP-1/glucagon receptor dual agonist for the prevention or treatment of non-alcoholic fatty liver disease.

The composition of the present invention is characterized by either having no side effect of weight gain or reducing the side effect of weight gain.

Furthermore, the composition of the present invention can prevent or treat non-alcoholic fatty liver disease by performing at least one of the following functions: (a) reducing the expression or activity of collagen-1a, which is a fibrosis marker; (b) reducing the expression or activity of tumor necrosis factor-α (TNF-α), which is a pro-inflammatory marker; (c) reducing the expression or activity of sterol regulatory element binding protein-1c (SREBP-1c), which is a lipogenesis marker; (d) reducing liver triglycerides; and (e) reducing blood cholesterol.

Figure 2:
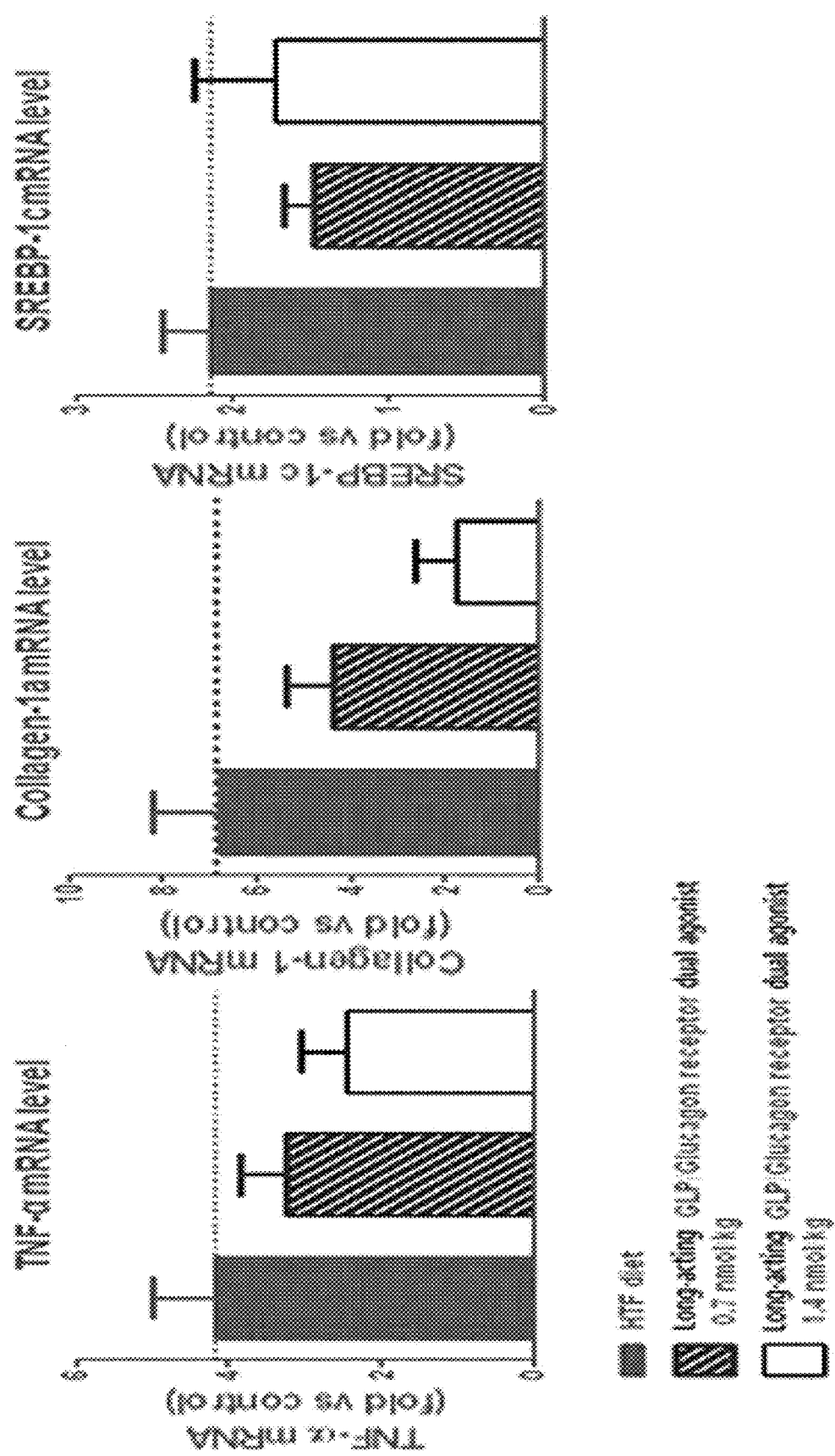
FIG. 2 is a graph showing the results of measuring collagen-1a, TNF-α, SREBP-1c mRNA of the long-acting GLP-1/glucagon receptor dual agonist in the high-fat, fructose and cholesterol containing high trans-fat feed intake ob/ob mouse model.
Figure 3:
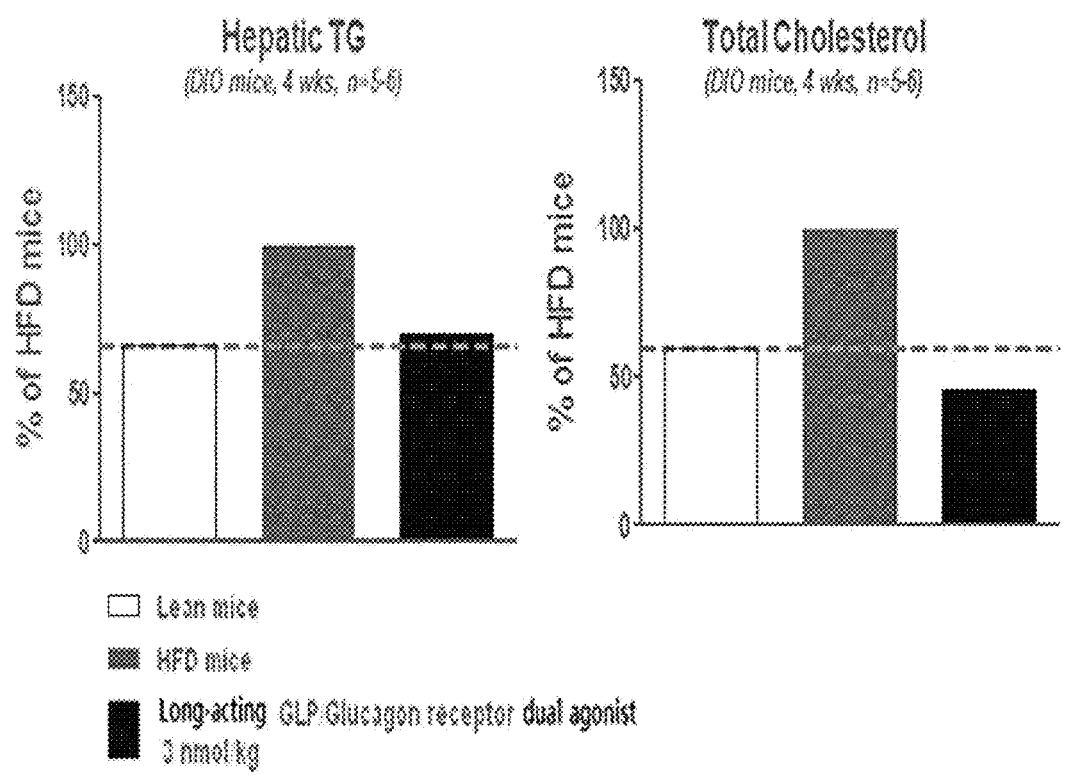
FIG. 3 is a graph showing the reduction of the content of the liver triglyceride and serum cholesterol of the long-acting GLP-1/glucagon receptor dual agonist in the high trans-fat feed intake DIO mouse model.

In one embodiment of the present invention, the long-acting GLP-1/glucagon receptor dual agonist of the present invention was administered to various animal models of non-alcoholic fatty liver disease. As a result, it was confirmed that the body weight and liver weight were significantly decreased compared to those of a non-treated group (FIG. 1) and that there was no side-effect such as weight gain as in the use of a conventional therapeutic agent. Furthermore, it was confirmed that the expression of collagen-1a, TNF-α, SREBP-1c decreased remarkably compared to that of the non-treated group, thus preventing fibrosis, i.e., of hepatic fibrosis, inhibiting inflammation, and inhibiting fat accumulation inhibition (FIG. 2). Therefore, it was confirmed that the long-acting GLP-1/glucagon receptor dual agonist of the present invention can be used as a drug for the prevention and treatment of various non-alcoholic liver diseases. In addition, it was confirmed that liver triglycerides and blood cholesterol was significantly reduced compared to those of the non-treated group and that they were significantly reduced to a normal animal level (FIG. 3). Therefore, it was confirmed that the long-acting GLP-1/glucagon receptor dual agonist of the present invention can be used as an excellent drug for the prevention and treatment of various non-alcoholic liver diseases.

As used herein, the term "GLP-1/glucagon receptor dual agonist" may be used interchangeably with a "GLP-1/glucagon dual agonist". The GLP-1/glucagon receptor dual agonist includes all peptides, or fragments, precursors, derivatives or variants thereof which have GLP-1/glucagon dual activity, like oxyntomodulin, a native GLP-1/glucagon receptor dual agonist, and also materials that can activate the GLP-1 and glucagon receptor at the same time, but is not limited thereto. In the present invention, the GLP-1/glucagon receptor agonist may be a receptor dual-dual agonist applying the long-acting technique to overcome the short half-life, and preferably a long-acting receptor dual agonist which can be administered once a week, but is not limited thereto. Specific examples of the GLP-1/glucagon receptor dual agonist according to the present invention partially may include, for example, the GLP-1/glucagon receptor dual agonist, a derivative thereof, and a long-acting type thereof as described in Korean Patent Application Publication Nos. 10-2012-0137271 and 10-2012-0139579, whose entire contents are incorporated herein by reference.

In one embodiment of the present invention, the long-acting GLP-1/glucagon receptor dual agonist may be in a conjugate form, wherein a biocompatible material or a carrier is linked to the agonist by a covalent bond or a linker. In another embodiment, such long-acting type may be in a form, wherein a biocompatible material or a carrier can be linked directly to the GLP-1/glucagon receptor dual agonist by a covalent bond by a known genetic recombination technique. The long-acting type of the mentioned GLP-1/glucagon receptor dual agonist can improve the half-life or bioavailability compared to a form in which the sequence of the GLP-1/glucagon receptor dual agonist is not the long-acting type but is otherwise the same. In accordance with one embodiment of the present invention, as one example of the long-acting GLP-1/glucagon receptor dual agonist, a composition in which the immunoglobulin Fc region is linked to the 30th amino acid of the GLP-1/glucagon receptor dual agonist by the non-peptide polymer linker, preferably PEG, may be used, but is not limited thereto.

As used herein, the term "biocompatible material" or "carrier" refer to materials which can increase the duration of the activity of the GLP-1/glucagon receptor dual agonist when the biocompatible material and the carrier are covalently or noncovalently linked to the GLP-1/glucagon receptor dual agonist of the present invention directly or indirectly to form a conjugate. For example, when forming the conjugate, a material which can increase the in vivo half-life of the GLP-1/glucagon receptor dual agonist may be a biocompatible material or carrier according to the present invention. The type of the biocompatible material or carrier that can be used to increase the half-life varies, and examples thereof may include polyethylene glycol, fatty acid, cholesterol, albumin and a fragment thereof, an albumin-binding substance, a polymer of repeating units of a specific amino acid sequence, an antibody, an antibody fragment, an Fc neonatal receptor (FcRn) binding material, an in vivo connective tissue, a nucleotide, fibronectin, transferrin, a saccharide, a polymer, etc. Of course, the carriers or biocompatible materials may be used in combination of at least two thereof. The biocompatible material or carrier includes a biocompatible material that extends the in vivo half life through a covalent or non-covalent bond.

In the present invention, the methods in which the biocompatible material or the carrier are linked to the GLP-1/glucagon receptor dual agonist include a genetic recombination method and an in vitro linkage using polymers or low molecular chemicals, but are not limited thereto. The FcRn binding material may be an immunoglobulin Fc region. For example, when polyethylene glycol is used as the carrier, there may be included a Recode technique by Ambrx Inc., which can attach position-specifically to polyethylene glycol. The methods may include a glycopegylation technique by Neose company which can attach specifically to the glycosylated moiety. Furthermore, the methods may include a releasable PEG technique in which polyethylene glycol is removed, but is not limited thereto. The methods may include techniques which can increase bioavailability using PEG. In addition, polymers such as polyethylene glycol, polypropylene glycol, ethylene glycol-propylene glycol copolymer, polyoxyethylated polyol, polyvinyl alcohol, polysaccharides, dextran, polyvinyl ethyl ether, biodegradable polymer, lipid polymer, chitins, or hyaluronic acid may be included.

When albumin is used as a carrier, the methods may include a technology in which albumins or albumin fragments can be directly covalently linked to peptides of the GLP-1/glucagon receptor dual agonist to increase the in vivo stability. Even if albumin is not directly linked, there may be included a technique in which the albumin binding materials, for example, albumin-specific binding antibody or an antibody fragment are bound to the peptides to bind to the albumin, and a technique in which a certain peptide/protein having a binding affinity to albumin is bound to the peptides. In addition, the methods may include a technique in which a fatty acid, etc., having a binding affinity to albumin is bound to the peptides, but is not limited thereto. Any technique or binding method which can increase the in vivo stability using albumin may be included herein.

The technique for binding to the peptide by using the antibody or antibody fragment as a carrier in order to increase the in vivo half-life may also be included in the present invention. The antibody or antibody fragment having a FcRn binding site can be used, and any antibody fragment not containing FcRn binding site such as Fab can be used. CovX-body technique of CovX company using a catalytic antibody may be included herein, and the technique which increases the in vivo half-life using Fc fragments may be included in the present invention. When using the Fc fragment, the linker binding to the Fc fragment and the peptide and its binding method may include a peptide bond or a polyethylene glycol or the like, but is not limited to thereto and any chemical binding method may be applicable. In addition, the binding ratio of the GLP-1/glucagon receptor agonists dual agonist of the present invention may be 1:1 or 1:2, but is not limited thereto, and any ratio which can increase the in vivo half-life may be included without limitation.

Further, the carrier which is used to increase the in vivo half-life may be a non-peptidyl material such as a polysaccharide or a fatty acid.

The linker binding to the carrier which is used to increase the in vivo half-life may include peptides, polyethylene glycols, fatty acids, sugars, polymers, low molecular compounds, nucleotides, and a combination thereof, and may be any chemical bond such as a non-covalent chemical bond, a covalent chemical bond, etc., without limitation.

The formulation which can increase the bioavailability or continuously maintain the activity may include a sustained release formulation by microparticles, nanoparticles and the like using PLGA, hyaluronic acid, chitosan, etc.

Furthermore, the formulation of different aspects which can increase the bioavailability or continuously maintain the activity may be a formulation such as implants, inhalants, transnasal formulations or patches.

In one exemplary embodiment of the invention, examples of the GLP-1/glucagon receptor dual agonist can include a native GLP-1/glucagon receptor dual agonist such as oxyntomodulin and the derivatives thereof, the long-acting formulation thereof, and the like can also be included.

As used herein, the term "oxyntomodulin" means a peptide derived from a glucagon precursor, pre-glucagon, and includes a native oxyntomodulin, precursors, derivatives, fragments thereof, and variants thereof. Preferably, it can have the amino acid sequence of SEQ ID NO. 1 (HSQGTFTSDYSKYLDSRRAQDFVQWLMNTKRNRNNIA).

The term, "oxyntomodulin variant" is a peptide having one or more amino acid sequences different from those of native oxyntomodulin, and means a peptide that retains the function of activating the GLP-1 and glucagon receptors, and it may be prepared by any one of substitution, addition, deletion, and modification or by a combination thereof in a part of the amino acid sequences of the native oxyntomodulin.

The term, "oxyntomodulin derivative" includes peptides, peptide derivatives or peptide mimetics that are prepared by addition, deletion or substitution of amino acids of oxyntomodulin so as to activate both of the GLP-1 receptor and the glucagon receptor at a high level, compared to the native oxyntomodulin. Preferably, the oxyntomodulin derivative has an amino acid sequence of SEQ ID No. 25 and more preferably, its $16^{th}$ and $20^{th}$ amino acids form a ring.

The term, "oxyntomodulin fragment" means a fragment having one or more amino acids added or deleted at the N-terminus or the C-terminus of the native oxyntomodulin, in which non-naturally occurring amino acids (for example, D-type amino acid) can be added, and has a function of activating both of the GLP-1 receptor and the glucagon receptor.

Each of the preparation methods for the variants, derivatives, and fragments of oxyntomodulin can be used individually or in combination. For example, the present invention includes a peptide that has one or more amino acids different from those of native peptide and deamination of the N-terminal amino acid residue, and has a function of activating both of the GLP-1 receptor and the glucagon receptor.

The C-terminal of the variants, derivatives, and fragments of oxyntomodulin of the present invention may be amidated.

The carrier material which may be used in the present invention may be selected from the group consisting of an antibody, an immunoglobulin Fc region, an albumin, a fatty acid, a carbohydrate, a polymer having a repeating unit of a peptide, a transferrin, and a PEG, and preferably an immunoglobulin Fc region. In one exemplary embodiment of the present invention, the long-acting GLP-1/glucagon receptor dual agonist is linked to a carrier by the non-peptidyl polymer as a linker. In one more exemplary embodiment, a carrier linked to a non-peptidyl polymer is an immunoglobulin Fc fragment.

In the present invention, the long-acting GLP-1/glucagon receptor dual agonist is a form in which the GLP-1/glucagon receptor dual agonist is each linked to an immunoglobulin Fc region, and shows the sustainability and safety. Binding of the immunoglobulin Fc region and the GLP-1/glucagon receptor dual agonist may be an inframe fusion without a linker or may be linked using a non-peptide polymer linker. In the present invention, the immunoglobulin Fc may be used interchangeably with immunoglobulin fragments.

As used herein, the term "non-peptidyl polymer" refers to a biocompatible polymer including at least two repeating units linked to each other by any covalent bond excluding a peptide bond. In the present invention, the non-peptidyl polymer may be interchangeably used with the non-peptidyl linker.

The non-peptidyl polymer that may be used in the present invention may be selected from the group consisting of a biodegradable polymer such as polyethylene glycol, polypropylene glycol, ethylene glycol-propylene glycol copolymer, polyoxyethylated polyol, polyvinyl alcohol, polysaccharide, dextran, polyvinyl ethyl ether, polylactic acid (PLA) or polylactic-glycolic acid (PLGA), a lipid polymer, chitin, hyaluronic acid, and a combination thereof, and preferably, the biodegradable polymer is polyethylene glycol. In addition, derivatives thereof known in the art and derivatives easily prepared by a method known in the art may be included in the scope of the present invention.

The peptide linker which is used in the fusion protein obtained by a conventional inframe fusion method has a disadvantage in that it is easily cleaved in vivo by a protease, and thus a sufficient effect of increasing the serum half-life of the active drug by a carrier cannot be obtained as expected. However, in the present invention, the polymer having resistance to the protease may be used to maintain the serum half-life of a peptide similarly as the carrier. Therefore, any non-peptidyl polymer may be used without limitation, as long as it is a polymer having the mentioned function, that is, a polymer having resistance to the in vivo protease. The non-peptidyl polymer has a molecular weight in the range of 1 to 100 kDa, and preferably of 1 to 20 kDa. Further, the non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug. The reactive group at both ends of the non-peptidyl polymer is preferably selected from the group consisting of a reactive aldehyde group, a propionaldehyde, a butyraldehyde group, a maleimide group, and a succinimide derivative. The succinimide derivative may be succinimidyl propionate, hydroxy succinimidyl, succinimidyl carboxymethyl, or succinimidyl carbonate. In particular, when the non-peptidyl polymer has a reactive group of the reactive aldehyde group at both ends thereof, it is effective to minimize nonspecific reactions and link a physiologically active polypeptide and an immunoglobulin at both ends of the non-peptidyl polymer. A final product produced by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0. The reactive groups at both ends of the non-peptidyl polymer may be the same or different from each other. For example, the non-peptidyl polymer may possess a maleimide group at one end, and an aldehyde group, a propionaldehyde group, or a butyraldehyde group at the other end. When a polyethylene glycol having a reactive hydroxy group at both ends is used as the non-peptidyl polymer, the hydroxy group may be activated to various reactive groups by known chemical reactions, or a commercially available polyethylene glycol having a modified reactive group may be used to prepare the long acting GLP-1/glucagon receptor dual agonist conjugate of the present invention.

In addition, the immunoglobulin Fc region is advantageous in terms of the preparation, purification, and yield of the conjugate, because not only the molecular weight is relatively small compared to the entire molecule, but the homogeneity of the materials is also greatly increased and the potential of inducing antigenicity in blood is lowered, because the amino acid sequences are different in each antibody, and thus the Fab portion showing a high non-homogeneity is removed.

As used herein, the term "immunoglobulin Fc region" refers to the heavy-chain constant region 2 (CH2) and the heavy-chain constant region 3 (CH3) of an immunoglobulin, excluding the variable regions of the heavy and light chains, the heavy-chain constant region 1 (CH1), and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains of the immunoglobulin, as long as it has an effect substantially equivalent to or better than the native protein. Furthermore, the immunoglobulin Fc region may be a fragment having a deletion of a relatively long portion of the amino acid sequence which corresponds to CH2 and/or CH3. That is, the immunoglobulin Fc region of the present invention may comprise 1) a CH1 domain, a CH2 domain, a CH3domain, and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

Further, the immunoglobulin Fc region of the present invention includes a native amino acid sequence as well as a sequence derivative (mutant) thereof. An amino acid sequence derivative has a different sequence due to a deletion, an insertion, a non-conservative or conservative substitution, or combinations thereof of one or more amino acid residues of the native amino acid sequences. For example, in an IgG Fc, amino acid residues at positions 214 to 238, 297 to 299, 318 to 322, or 327 to 331, known to be important in binding, may be used as a suitable target for modification.

Further, various kinds of derivatives are possible, including one in which a region capable of forming a disulfide bond is deleted, certain amino acid residues are eliminated at the N-terminal end of a native Fc, a methionine residue is added to the N-terminal end of a native Fc, etc. Further, to remove effector functions, a complement-binding site, such as a Clq-binding site, and an antibody dependent cell mediated cytotoxicity (ADCC) site may be deleted. Techniques of preparing such sequence derivatives of the immunoglobulin Fc region are disclosed in International Publication Nos: WO 97/34631, WO 96/32478, etc. Amino acid exchanges in proteins and peptides, which do not entirely alter the activity of the molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/

Gly, Thy/Phe, Ala/Pro, Lys/Arg, Asp/Asn, Leu/Ile, Leu/Val, Ala/Glu, and Asp/Gly, in both directions. In addition, the Fc region, if desired, may be modified by phosphorylation, sulfation, acrylation, glycosylation, methylation, farnesylation, acetylation, amidation, and the like.

The Fc derivatives are derivatives that have a biological activity identical to the Fc region of the present invention, with improved structural stability of the Fc region, for example, against heat, pH or the like.

Furthermore, these Fc regions may be obtained from native forms isolated from humans and other animals including cows, goats, pigs, mice, rabbits, hamsters, rats, guinea pigs, etc., or may be recombinants or derivatives thereof, obtained from transformed animal cells or microorganisms. Herein, they may be obtained from a native form by isolating whole immunoglobulins from human or animal organisms and then treating them with a protease. When papain is treated, papain digests the native immunoglobulin into Fab and Fc regions, and when pepsin is treated, the native immunoglobulin is cut into pF'c and F(ab)2. Fc or pF'c may be isolated by size exclusion chromatography, etc. Preferably, a human-derived Fc region is a recombinant immunoglobulin Fc region that is obtained from a microorganism.

In addition, the immunoglobulin Fc region may be in the form of having native sugar chains, or increased or decreased sugar chains compared to a native form, or may be in a deglycosylated form. The increase, decrease, or removal of the immunoglobulin Fc sugar chains may be achieved by methods common in the art, such as a chemical method, an enzymatic method and a genetic engineering method using a microorganism. The removal of sugar chains from an Fc region results in a remarkable decrease in binding affinity to the C1q part and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable for the objective of the present invention as a drug carrier.

As used herein, the term "deglycosylation" refers to enzymatically removing sugar moieties from an Fc region, and the term "aglycosylation" refers to an Fc region which is produced in a prokaryote, preferably *E. coli*, and is not glycosylated.

Meanwhile, the immunoglobulin Fc region may be derived from humans or other animals including cows, goats, pigs, mice, rabbits, hamsters, rats, guinea pigs, etc., and preferably from humans.

Also, the immunoglobulin Fc region may be an Fc region that is derived from IgG, IgA, IgD, IgE and IgM, a combination thereof, or hybrids thereof. Preferably, it is derived from IgG or IgM which are the most abundant in human blood, and most preferably from IgG, which is known to enhance the half-lives of ligand-binding proteins, but is not limited thereto.

As used herein, the term "combination" refers to that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

As used herein, the term "hybrid" refers to that a sequence corresponding to at least two Fc fragments of a different origin is present in a single-chain immunoglobulin Fc region. In the present invention, various types of hybrid are possible. That is, the hybrid consisting of 1 to 4 domains selected from the group consisting of CH1, CH2, CH3 and CH4 of IgG Fc, IgM Fc, IgA Fc, IgE Fc and IgD Fc is possible, and may include a hinge.

On the other hand, IgG may also be classified into IgG1, IgG2, Ig3, and IgG4 sub-classes, and in the present invention, a combination or hybridization thereof is possible. It is preferably IgG2 and IgG4 sub-classes, and most preferably is a Fc region of IgG4 that substantially does not have an effector function such as a complement dependent cytotoxicity (CDC).

That is, the immunoglobulin Fc region for the carrier of the drug of the present invention may be, for example, human IgG4-derived aglycosylated Fc region, but is not limited thereto. The human-derived Fc region is preferred over nonhuman-derived Fc region which can cause undesirable immune responses, for example, which can act as an antigen in the human body to produce a new antibody.

The method for preparing a long-acting GLP-1/glucagon receptor dual agonist of the present invention is not particularly limited. For example, details of the preparation method and its effects are described, for example, in Korean Patent Application Publication No. 10-2012-0139579.

Using the long-acting GLP-1/glucagon receptor dual agonist has huge advantages of that the number of administration to a chronic patient who needs daily administration can be dramatically reduced due to an increase in the blood half-life and in vivo sustainability, thereby improving the quality of life of the patient. Therefore, this is very helpful in the treatment of non-alcoholic fatty liver disease.

As used herein, the term "non-alcoholic fatty liver disease" refers to fatty liver cases in which there is no history of alcohol consumption or in which alcohol consumption is not related to the occurrence. The fatty liver refers to a phenomenon in which there is abnormal accumulation of triglyceride in liver cells, compared to normal levels of triglyceride. About 5% of normal liver consists of fat tissue and the main components of the fat are triglycerides, fatty acids, phospholipids, cholesterols, and cholesterol esters. However, once the fatty liver occurs, most of the components are replaced with triglyceride. If the amount of triglycerides is more than 5% of the liver weight, it is diagnosed as fatty liver. The fatty liver is caused by a lipid metabolism disorder or a defect in the process of carrying excessive fat in the liver cells, and is mainly caused by disorders of lipid metabolism in the liver. Most of the fat accumulated in the fatty liver may be a triglyceride. The non-alcoholic fatty liver disease includes non-alcoholic fatty liver, nonalcoholic steatohepatitis, cirrhosis, liver cancer, and the like, but the fatty liver disease to be prevented or treated with the composition of the present invention is included without limitation.

As used herein, the term "prevention" refers to all of the actions by which the non-alcoholic fatty liver disease is prevented or delayed by administration of the composition of the present invention. The "treatment" refers to all of the actions by which the symptoms of the non-alcoholic fatty liver disease are alleviated, or positively changed. The treatment of the non-alcoholic fatty liver disease is applicable to any mammal that may experience the non-alcoholic fatty liver disease, and examples thereof include not only humans and primates, but also cattle such as cow, pig, sheep, horse, dog and cat, without limitation, but is preferably a human.

As used herein, the term "administration" refers to introduction of an amount of a predetermined substance to a patient by a suitable method. The composition of the present invention may be administered via any of the common routes, as long as it is able to reach a desired tissue. For example, it may be intraperitoneal, intravenous, intramuscular, subcutaneous, intradermal, oral, topical, intranasal, intrapulmonary, or intrarectal administration, but is not limited thereto. However, since peptides are digested upon oral administration, active ingredients of a composition for oral administration should be coated or formulated for protection against degradation in the stomach. Preferably, the composition may be administered in the form of injections. In addition, the long-acting formulation may be administered by any apparatus in which an active material can be transported into a target cell.

The administration dose and frequency of the pharmaceutical composition of the present invention are determined by the type of active ingredient, together with various factors such as the disease to be treated, administration route, patient's age, gender, and body weight, and disease severity.

The pharmaceutical composition of the present invention may further include a pharmaceutically acceptable carrier, excipient, or diluent. As used herein, the term "pharmaceutically acceptable carrier" refers to a carrier or a diluent that does not stimulate the organism and inhibit biological activity or characteristics of an administered compound. For oral administration, the carrier may include a binder, a lubricant, a disintegrant, an excipient, a solubilizer, a dispersing agent, a stabilizer, a suspending agent, a colorant, and a flavoring agent. For injectable preparations, the carrier may include a buffering agent, a preserving agent, an analgesic, a solubilizer, an isotonic agent, a stabilizer, etc. For preparations for topical administration, the carrier may include a base, an excipient, a lubricant, a preserving agent, etc.

The composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calciumphosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

In another aspect, the present invention provides a method for preventing or treating a non-alcoholic liver disease, comprising a step of administering the composition comprising the long-acting GLP-1/glucagon receptor dual agonist to a subject, exclusive of humans, at high risk of or having the non-alcoholic liver disease.

The description of the composition and non-alcoholic fatty liver disease is the same as above.

MODE FOR THE INVENTION

Hereinafter, the present invention will be described in more detail by way of examples. These examples are only intended to illustrate the present invention, and the scope of the present invention is not construed as being limited to these examples.

EXAMPLE 1

Synthesis of Oxyntomodulin Derivatives

In the examples, oxyntomodulin derivatives having the following amino acid sequences were synthesized (Table 1).

TABLE 1

[Table 1]
Oxyntomodulin and oxyntomodulin derivatives

| SEQ ID NO. | Amino acid sequence |
|---|---|
| SEQ ID NO. 1 | HSQGTFTSDYSKYLDSRRAQDFVQWLMNTKRNRNNIA |
| SEQ ID NO. 2 | CA-SQGTFTSDYSKYLDEEAVRLFIEWLMNTKRNRNNIA |
| SEQ ID NO. 3 | CA-SQGTFTSDYSKYLDERRAQDFVAWLKNTGPSSGAPPPS |
| SEQ ID NO. 4 | CA-GQGTFTSDYSRYLEEEAVRLFIEWLKNGGPSSGAPPPS |
| SEQ ID NO. 5 | CA-GQGTFTSDYSRQMEEEAVRLFIEWLKNGGPSSGAPPPS |
| SEQ ID NO. 6 | CA-GEGTFTSDLSRQMEEEAVRLFIEWAAHSQGTFTSDYSKYLD |
| SEQ ID NO. 7 | CA-SQGTFTSDYSRYLDEEAVRLFIEWLMNTK |
| SEQ ID NO. 8 | CA-SQGTFTSDLSRQLEEEAVRLFIEWLMNK |
| SEQ ID NO. 9 | CA-GQGTFTSDYSRYLDEEAVXLFIEWLMNTKRNRNNIA |
| SEQ ID NO. 10 | CA-SQGTFTSDYSRQMEEEAVRLFIEWLMNGGPSSGAPPPSK |
| SEQ ID NO. 11 | CA-GEGTFTSFLSRQMEEEAVRLFIEWAAHSQGTFTSDYSRYLDK |
| SEQ ID NO. 12 | CA-SQGTFTSDYSRYLDGGGHGEGTFTSDLSKQMEEEAVK |
| SEQ ID NO. 13 | CA-SQGTFTSDYSRYLDXEAVXLFIEWLMNTK |
| SEQ ID NO. 14 | CA-GQGTFTSDYSRYLDEEAVXLFIXWLMNTKRNRNNIA |
| SEQ ID NO. 15 | CA-GQGTFTSDYSRYLDEEAVRLFIXWLMNTKRNRNNIA |
| SEQ ID NO. 16 | CA-SQGTFTSDLSRQLEGGGHSQGTFTSDLSRQLEK |
| SEQ ID NO. 17 | CA-SQGTFTSDYSRYLDEEAVRLFIEWIRNTKRNRNNIA |
| SEQ ID NO. 18 | CA-SQGTFTSDYSRYLDEEAVRLFIEWIRNGGPSSGAPPPSK |
| SEQ ID NO. 19 | CA-SQGTFTSDYSRYLDEEAVKLFIEWIRNTKRNRNNIA |
| SEQ ID NO. 20 | CA-SQGTFTSDYSRYLDEEAVKLFIEWIRNGGPSSGAPPPSK |

TABLE 1-continued

[Table 1]
Oxyntomodulin and oxyntomodulin derivatives

| SEQ ID NO. | Amino acid sequence |
|---|---|
| SEQ ID NO. 21 | CA-SQGTFTSDYSRQLEEEAVRLFIEWVRNTKRNRNNIA |
| SEQ ID NO. 22 | DA-SQGTFTSDYSKYLDEKRAKEFVQWLMNTK |
| SEQ ID NO. 23 | HAibQGTFTSDYSKYLDEKRAKEFVCWLMNT |
| SEQ ID NO. 24 | HAibQGTFTSDYSKYLDEKRAKEFVQWLMNTC |
| SEQ ID NO. 25 | HAibQGTFTSDYSKYLDEKRAKEFVQWLMNTC |
| SEQ ID NO. 26 | HAibQGTFTSDYSKYLDEKRAKEFVQWLMNTC |
| SEQ ID NO. 27 | HAibQGTFTSDYSKYLDEQAAKEFICWLMNT |
| SEQ ID NO. 28 | HAibQGTFTSDYSKYLDEKRAKEFVQWLMNT |
| SEQ ID NO. 29 | H(d)SQGTFTSDYSKYLDSRRAQDFVQWLMNTKRNRNNIA |
| SEQ ID NO. 30 | CA-SQGTFTSDYSKYLDSRRAQDFVQWLMNTKRNRNNIA |
| SEQ ID NO. 31 | CA-(d)SQGTFTSDYSKYLDSRRAQDFVQWLMNTKRNRNNIA |
| SEQ ID NO. 32 | CA-AibQGTFTSDYSKYLDEKRAKEFVQWLMNTC |
| SEQ ID NO. 33 | HAibQGTFTSDYAKYLDEKRAKEFVQWLMNTC |
| SEQ ID NO. 34 | YAibQGTFTSDYSKYLDEKRAKEFVQWLMNTC |

In Table 1, amino acids in bold and underlined represent ring formation, and amino acids represented by X mean a non-native amino acid, alpha-methyl-glutamic acid. In addition, CA represents 4-imidazoacetyl, and DA represents desamino-histidyl.

Hereafter, a representative long-acting GLP-1/glucagon receptor dual agonist, i.e., the long-acting GLP-1/glucagon receptor dual agonist in which Fc is linked to the 30th amino acid of the GLP-1/glucagon receptor dual agonist by the non-peptidyl polymer, PEG (polyethylene glycol), was prepared and used in Examples 2 to 3 below.

EXAMPLE 2

Confirmation of the Effects of the Long-Acting GLP-1/Glucagon Receptor Dual Agonist on Non-Alcoholic Fatty Liver Disease in the High-Fat. Fructose and Cholesterol Containing High Trans-Fat Feed Intake Ob/Ob Mouse Model In order to confirm the effects of the long-acting GLP-1/glucagon receptor dual agonist on non-alcoholic fatty liver disease, a high-fat (40% kcal), fructose (22%) and cholesterol (2%)-containing high trans-fat diet (HTF diet) was taken to administrated to ob/ob mouse model for 8 weeks to prepare an animal model for non-alcoholic fatty liver disease. Then, the long-acting GLP-1/glucagon receptor dual agonist was subcutaneously administered to the mouse once every two days (Q2D) with 0.7 and 1.4 nmol/kg and the administration was repeated for 4 weeks. The weight of the animals was compared to that of the vehicle-treated group during the 4-week test. After completion of the 4 week-test, the liver weights were measured and compared. Further, after completion of the 4 week-test, mRNAs of, collagen-la, which is a fibrosis marker; TNF-α which is a pro-inflammatory marker; and SREBP-1c which is a lipogenesis marker were confirmed.

Figure 1:
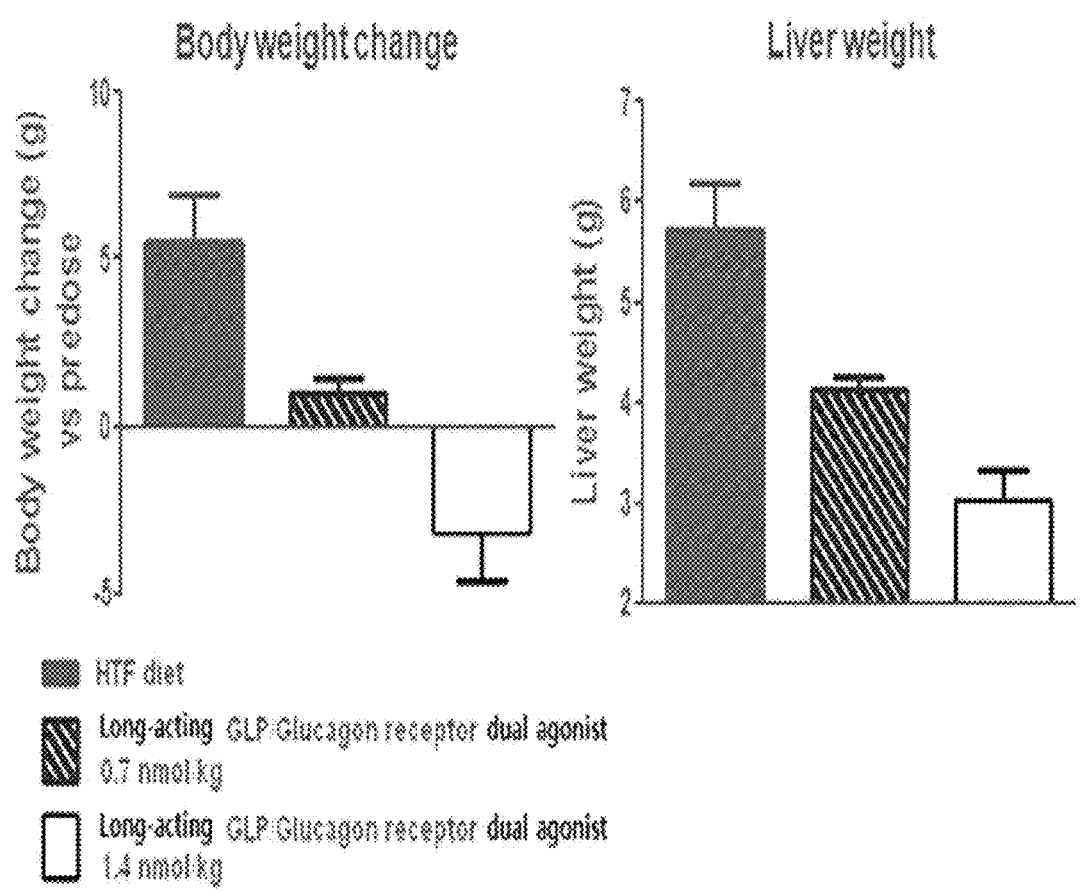
FIG. 1 is a graph showing changes in body weight and liver weight of the long-acting GLP-1/glucagon receptor dual agonist in the high-fat, fructose and cholesterol containing high trans-fat feed intake ob/ob mouse model.

As a result, the measurement of the body weight and the liver weight after administration for 4 weeks has shown that, in the long-acting GLP-1/glucagon receptor dual agonist, the weight was significantly reduced as compared to that of vehicle-treated group (FIG. 1). Such results suggest that the long-acting GLP-1/glucagon receptor dual agonist of the present invention can suppress the weight gain which occurs in the animal model for non-alcoholic fatty liver disease and that it can reduce the side-effects of conventional drugs for improving insulin resistance.

Further, the comparison of mRNA of collagen-la, TNF-α, SREBP-1c has shown that in the long-acting GLP-1/glucagon receptor dual agonist-treated group, these mRNA were significantly reduced (FIG. 2). Such results suggest that the long-acting GLP-1/glucagon receptor dual agonist of the present invention reduces fibrosis, pro-inflammation and the like in the animal model for the non-alcoholic fatty liver disease and inhibit fat production, thus being effective for the prevention and treatment of non-alcoholic fatty liver disease.

EXAMPLE 3

Confirmation of the Effects of the Long-Acting GLP-1/Glucagon Receptor Dual Agonist on Non-Alcoholic Fatty Liver Disease in the High Trans-Fat Feed Intake DI0 Mouse Model In order to confirm the effects of the long-acting GLP-1/glucagon receptor dual agonist on the non-alcoholic fatty liver disease, a 60% high trans-fat diet was administered to normal mouse model (C57BL/6) for 12 weeks to prepare an animal model for non-alcoholic fatty liver disease. Then, 3 nmol/kg of the long-acting GLP-1/glucagon receptor dual agonist was subcutaneously administered to the mouse once every week (QW) and the administration was repeated for 4 weeks. After completion of the 4 week-test, hepatic triglyceride (hepatic TG) and serum cholesterol were measured.

As a result, the measurement of the hepatic triglycerides and serum cholesterol after administration for 4 weeks has shown that, in the case of administration of the long-acting GLP-1/glucagon receptor dual agonist, they were significantly reduced as compared to those of the vehicle-treated group and also that they were significantly reduced to the level of a normal animal which has undergone a chow diet (FIG. 3). Such results suggest that the long-acting GLP-1/glucagon receptor dual agonist of the present invention can reduce the hepatic triglyceride and serum cholesterol to normal animal levels in the animal model for the non-alcoholic fatty liver disease, thus being effective for the prevention and treatment of non-alcoholic fatty liver disease.

From the above description, a person skilled in the art will appreciate that the invention may be embodied in other specific forms without changing the technical spirit or essential characteristics. In this regard, the embodiments described above should be understood to be illustrative rather than restrictive in every respect. The scope of the invention should be construed that the meaning and scope of the appended claims rather than the detailed description and all changes or variations derived from the equivalent concepts fall within the scope of the present invention.

The invention claimed is:

1. A method for preventing or treating liver inflammation in a subject, comprising administering a long-acting glucagon-like peptide-1 (GLP-1)/glucagon receptor dual agonist conjugate to the subject, wherein the subject is at high risk of or has the liver inflammation, wherein the long-acting GLP-1/glucagon receptor dual agonist conjugate comprises:
   a GLP-1/glucagon receptor dual agonist comprising the amino acid sequence of any one of SEQ ID NOs: 2-23 or 27-34;
   an immunoglobulin Fc region; and
   a non-peptidyl polymer, wherein the non-peptidyl polymer covalently links the GLP-1/glucagon receptor dual agonist and the immunoglobulin Fc region.

2. The method of claim 1, wherein the long-acting GLP-1/glucagon receptor dual agonist has no side effect of weight gain or reduces the side effect of weight gain.

3. The method of claim 1, wherein the method reduces the expression or activity of tumor necrosis factor-α (TNF-α).

4. The method of claim 1, wherein the long-acting GLP-1/glucagon receptor dual agonist simultaneously activates GLP-1 receptor and glucagon receptor.

5. The method of claim 1, wherein the amino acids at positions 12 and 16 or 16 and 20 of the long-acting GLP-1/glucagon receptor dual agonist form a ring.

6. The method of claim 1, wherein the non-peptidyl polymer comprises polyethylene glycol, polypropylene glycol, an ethylene glycol-propylene glycol copolymer, a polyoxyethylated polyol, polyvinyl alcohol, a polysaccharide, polyvinyl ethyl ether, a biodegradable polymer, a lipid polymer, hyaluronic acid, or a combination thereof.

7. The method of claim 6, wherein the non-peptidyl polymer comprises polyethylene glycol.

8. The method of claim 6, wherein the polysaccharide comprises dextran, a chitin, or a combination thereof.

9. The method of claim 1, wherein the immunoglobulin Fc region is aglycosylated.

10. The method of claim 1, wherein the immunoglobulin Fc region comprises a CH1 domain, CH2 domain, CH3 domain, CH4 domain, or a combination thereof.

11. The method of claim 10, wherein the immunoglobulin Fc region further comprises a hinge region.

12. The method of claim 1, wherein the immunoglobulin Fc region is derived from IgG, IgA, IgD, IgE, or IgM.

13. The method of claim 1, wherein the immunoglobulin Fc region is a hybrid of domains from IgG, IgA, IgD, IgE, or IgM.

* * * * *